United States Patent [19]

Bhogal

[11] Patent Number: 4,808,404

[45] Date of Patent: Feb. 28, 1989

[54] LIVE VACCINE FOR COCCIDIOSIS UTILIZING COCCIDIAL SPOROZOITES

[75] Inventor: Balbir S. Bhogal, Midlothian, Va.

[73] Assignee: A. H. Robins Company, Inc., Richmond, Va.

[21] Appl. No.: 141,953

[22] Filed: Jan. 11, 1988

[51] Int. Cl.⁴ .................... A61K 35/68; A61K 39/002
[52] U.S. Cl. .......................................... 424/88; 424/93; 424/451; 424/456; 424/457; 435/182; 435/177; 435/258; 435/947
[58] Field of Search ................... 424/88, 93, 451, 456, 424/459; 435/182, 258, 177, 947

[56] References Cited

U.S. PATENT DOCUMENTS 4,639,372  1/1987  Murray et al. ........................ 530/403
4,724,145  2/1988  Murray ................................ 435/68

*Primary Examiner*—Johnnie R. Brown
*Assistant Examiner*—Garnette D. Draper

[57] ABSTRACT

Methods and compositions are disclosed for vaccinating warm-blooded animals against coccidiosis utilizing suspensions of excysted coccidial sporozoites in physiologically balanced medium containing water-soluble polymeric stabilizers selected from gels, gelatins, polysaccharide gums, cellulose or cellulose derivatives which extend viability or storage, additional extension of viability in storage being attained when the suspensions are finely divided and the polymeric stabilizers are hardened to form microcapsules.

15 Claims, No Drawings

LIVE VACCINE FOR COCCIDIOSIS UTILIZING COCCIDIAL SPOROZOITES

1. INTRODUCTION
2. BACKGROUND OF THE INVENTION
   2.1 Biology and Life Cycle of Coccidial Protozoa
   2.2 Prior Related Vaccines
   2.3 Problems Solved
3. SUMMARY OF THE INVENTION
   3.1 The Discovery
   3.2 General Preparation of the Vaccine
   3.3 The Method of Vaccination (Administration)
4. DEFINITIONS
   4.1 Oocyst
   4.2 Sporulated Oocyst and Sporocyst
   4.3 Encysted Oocyst and Encysted Sporocyst
   4.4 Sporozoite
   4.5 Excysted Sporozoite
   4.6 Capsule Wall Material
   4.7 Cross Linking Agents
   4.8 Water Soluble Polymeric Stabilizers
   4.9 Modified Capsule Wall
   4.10 Physiologically Balanced
   4.11 Suspension
5. DETAILED DESCRIPTION OF THE INVENTION
   5.1 Scope and Applicability
   5.2 Preparation 1. Excysted *E. tenella* Sporozoites
      5.2.1 General Procedure for Isolating Excysted Sporozoites
      5.2.2 Obtaining Precursor Sporulated Oocysts
      5.2.3 Excystation of Sporozoites and Buffered Solution Thereof
      5.2.4 Chromatographic Purification of Excysted Sporozoites
   5.3 Preparation 2. Suspension of Excysted *E. tenella* Sporozoites In Isotonic Buffered Aqueous Sodium Alginate Solution
      5.3.1 Tris Buffer Solution
      5.3.2 Buffered Sodium Alginate Solution
      5.3.3 CalfSerum Addition
      5.3.4 Buffered Sporozoite - Alginate Suspension
   5.4 Preparation 3. Microcapsules Containing Stabilized Excysted Sporozoites In Isotonic Buffered Aqueous Solution
      5.4.1 Calculations on Volume Ratios
      5.4.2 Preparation of Hardening Bath
      5.4.3 Description of Gas Flow Droplet Generator
      5.4.4 Preparation of Microcapsules Containing Sporozoites Suspended in Stabilizing Aqueous Solution
      5.4.5 Washing of Microcapsules with Saline
      5.4.6 Storage Tests Relative to Viability of Microencapsulated Sporozoites
   5.5 Example 1. Demonstration of Subclinical Infection With Microencapsulated *E. tenella* Sporozoites In Chickens
   5.6 Example 2. Demonstration of Vaccination Potential Against *E. tenella* Coccidia Using Microencapsulated Excysted Stabilized Sporozoites in Chickens
   5.7 Example 3. Demonstration of Vaccination Potential Against *E. tenella* Coccidia Using Microencapsulated Excysted Stabilized Sporozoites In Chickens
   5.8 Example 4. Stabilizing Effect of Sodium Alginate on *E. tenella* Sporozoites.
   5.9 Example 5. Vaccination Potential Using Microcapsules Having Capsule Wall Modified With Citrate.

1. INTRODUCTION

This invention is concerned with methods of vaccinating warm-blooded animals against coccidiosis disease and compositions therefor utilizing microencapsulated excysted live coccidial sporozoites suspended in stabilizing carriers which greatly extend life expectancy or shelf-life of the sporozoites. More particularly aqueous compositions containing water soluble polymeric stabilizers, and physiologically balanced as to isotonicity and pH for all components which are used as suspending medium and carriers for the sporozoites. The water soluble polymeric stabilizers used may be classed as gels, gelatins, cellulose, cellulose derivatives, and polysaccharide gums, especially water soluble alginate salts. Preferably these sporozoite suspensions containing a water soluble polymeric stabilizer are first finely divided and then the surface of the particles is hardened to form microcapsules leaving an internal suspension of sporozoites in the stabilizing aqueous medium.

2. BACKGROUND OF THE INVENTION 2.1 Biology and Life Cycle of Coccidial Protozoa Coccidial protozoa may infect and inhabit the gastrointestinal tract of most species of warm-blooded animals, most often and most seriously when the animals are penned or in concentrated groups. For the most part infection occurs with coccidial species specific to the animal host species and more than one coccidial species may infect a given host animal species. For example, seven major coccidial species are known to infect the chicken.

The life cycle of the coccidial parasite involves several complex stages. Under natural conditions the cycle begins with oral ingestion by the host animal of excrement from another animal of the same species having sporulated oocysts dispersed therein. The sporulated oocyst shell then breaks down by action of the digestive system of the host animal. For example when the host animal is a chicken the outer shell of the sporulated oocyst is broken down mechanically to liberate first the sporocysts and finally biochemically to liberate sporozoites which are the ultimate infective organism. Other stages in the cycle which follow redevelopment within about 7 days include schizont I, merozoite I, schizont II, merozoite II, gametocyte, gamete and completion of the cycle with oocyst formation.

More descriptively, in the instance of the chicken, natural infection with one of the important species of Eimeria, i.e., *Eimeria tenella* begins with ingestion of an overwhelming amount of the sporulated oocysts. Each sporulated *E. tenella* oocyst contains four sporocysts and each sporocyst contains two sporozoites. In the stomach, the sporulated oocysts rupture, freeing the sporocysts. The sporozoites are liberated from the sporocysts by enzymatic action and pass down the digestive tract. Each of the sporozoites eventually reach the cecal pouches where they enter epithelial cells of the cecal mucosa and start an asexual multiplication cycle. The details of the completion of the life cycle referred to above are well known in the art.

The rationale of vaccination with live sporozoites, in the present invention, is to set up a low level of infection (subclinical) during the first few days of life of the animal, e.g., a chicken, without slowing down the performance of the animal in terms of growth. The subclinical infection, thus established induces immunity, while the host, e.g., chicken, has the advantages of passive protection afforded by maternal antibodies. The maternal antibodies also help to down regulate infection, thus helping to decrease unnecessary parasite buildup in animal houses, which is critical for the success of a vaccine since the degree of severity of disease is directly proportional to the numbers of sporulated oocysts ingested by the host from its environment. Under field conditions chickens, e.g., have their maternal anitbodies reduced to very low levels by the third week and hence become susceptible to the parasite, if their immune system is not primed by vaccination. Without vaccination the challenge encountered by hosts is frequently devastating, especially to concentrated populations of animals resulting in death or illness and/or poor development or growth quality and subsequent economic loss to the animal grower.

2.2 Prior Related Vaccines

U.K. Patent Specification No. 2,008,404 describes a method of promoting the growth of poultry by feeding viable sporulated oocysts of coccidia to poultry. Similarly chickens have been said to be immunized against cecal coccidiosis with viable sporulated oocysts in the disclosure of U.S. Pat. No. 3,147,186.

An immunogenic composition for oral administration comprising live encysted protozoa such as coccidia is described in British Application No. 2,144,331A wherein encysted sporulated coccidial oocysts or encysted coccidial sporocysts embedded in a firm gel matrix were fed orally to the host animal such as a newly-hatched poultry chick. Gels based on alginate were used for the matrix.

Sharma, N.N. in The Journal of Parasitology Vol. 50, No. 4 (1984) pp. 509–517 describes unsuccessful immunization trails with sporulated viable oocysts of coccidia or with an impure mixture said to contain sporozoites along with oocysts and sporocysts of coccidia administered to chickens, orally, intravenously, intraperitoneally, intramuscularly or subcutaneously.

2.3 Problems Solved

Since the severity of disease is directly proportional to the number of sporulated oocysts in the field available for ingestion, existing vaccines based on either feeding sporulated oocyst or feeding microencapsulated oocyst have limited utility for the broiler chicken industry, in that the high numbers of oocysts available for ingestion from day one often causes severe infections. As a result, the use of oral vaccines as such often necessitates the use of anticoccidials. Therefore the use of sporulated oocysts as live vaccines have limited application. Additionally, sporozoites are ineffective in producing an infection when administered orally to chickens.

Heretofore unsuccessful attempts to create immunity with unprotected sporozoites by systemic innoculation have been made by Sharma, supra., where attempts to create infection with sporozoites have been confined to use of freshly excysted sporozoites inasmuch as methods have not previously been available to keep the sporozoites alive longer than a few days under refrigeration. Consequently vaccination using sporozoites was impractical commercially.

The preferred method of this invention of microencapsulating by finely dividing a suspension and hardening the water-soluble polymeric stabilizer to enclose a physiologically balanced suspension of sporozoites provides time flexibility as to when the vaccine must be used, since the lifetime (in terms of viability and infectivity) of the sporozoites is extended up to at least 5 weeks. The second method of this invention of using water-soluble polymeric stabilizer, preferably a water-soluble alginate salt to suspend sporozoites in a medium physiologically balanced with respect to isotonicity and pH has extended the lifetime of the sporozoites up to at least 2 weeks and thus also provides time flexibility as to when the vaccine must be used.

The technique of microencapsulation of sporozoites used here not only provides a practical way of vaccination of chickens when they are handled on their first day of life, but also offers other advantages, such as, e.g., avoiding buildup of oocysts in the animal yard or pen which occurs both during vaccination as well as afterwards due to parasite multiplication in the host when live oocysts are used commercially, e.g., spread in the yard or pen or used in feed to innoculate, and thus avoids early overwhelming challenge due to that source of oocysts. Use of alginate suspension and microcapsules containing suspensions of sporozoites, in contrast, results in much slower and lower levels of oocyst buildup underfoot.

3.

SUMMARY OF THE INVENTION

3.1 The Discovery

The sporozoites of Elimeria species once out of their protective shells, i.e., oocysts and sporocysts, are very fragile and lose their infectivity within a few days. This invention is based on the discovery that Elimeria sporozoites can be kept alive for at least 5 weeks by microencapsulation and that the longevity of live excysted sporozoites can be increased to at least 2 weeks by addition of buffered equeous suspensions of the sporozoites the solutions of water soluble polymeric stabilizers including sodium alginate. The microencapsulation of live sporozoites provides a buffered viscous aqueous medium for the parasite consisting of a solution of water soluble polymeric stabilizer, said stabilizer preferably being sodium alginate. The microcapsules containing the aged sporozoites can be administered to baby chicks to establish subclinical infections thereby vaccinating against any future overwhelming challenge of *E. tenella* oocysts. Similar effective vaccination of chickens substituting other species of coccidia natural to the chicken and similar vaccination of other animals including poultry substituting viable excysted coccidial sporozoites appropriate to the animal species are reasonable expectations. Similar effective vaccinations with unencapsulated sporozoite buffered suspensions containing the water soluble polymeric stabilizers are also reasonable expectations.

3.2 General Preparation of the Vaccine

Purified, excysted live coccidial sporozoites are first obtained in a suspension of isotonic buffered aqueous solution by known procedures which involve mechanical, chemical and enzymatic breakdown of sporulated coccidial oocysts and sporocysts to remove the sporecase covers therefrom followed by chromatographic purification. Isotonic buffered sporozoite suspensions are added to solutions of protective agents (isotonic buffered polymeric stabilizers) which delay the death of the sporozoites and thereby extend the length of time the sporozoites remain viable in storage, such suitable protective agents being selected from hydrocolloids, gelatins, cellulose, cellulose derivatives and polysaccharides, especially alkali-metal alginate salts. Preferably the suspension so obtained is finely divided as a spray and mixed with hardening agent to give microcapsules which surround or contain the suspension of live excysted sporozoites in isotonically buffered medium.

3.3 Method of Vaccination (Administration)

According to the vaccination method of the invention, the isotonic buffered sporozoite suspension containing the protective agent, microencapsulated or unencapsulated, is administered to warm blooded animals to protect against severe damage to intestinal organs due to overwhelming challenge of coccidial oocysts. The microencapsulated preparations may be stored for at least 5 weeks. Although the preferred method is microencapsulation, the unencapsulated preparations may be stored for at least 2 weeks before using when kept refrigerated, but not frozen. Young animals, are treated with preparations carrying a quantified number of the excysted microencapsulated sporozoites appropriately chosen for the animal species involved. While any route of administration may be used, the subcutaneous route is preferred particularly for fowl.

4.

DEFINITIONS

Certain terms used in the present discussion should at this point be mentioned to assure that the reader is of the same mind as the author as to their respective meanings. Thus the following definitions are provided to clarify the scope of the present invention and to enable its formulation and use.

4.1 An "oocyst" is the dormant life-cycle stage of the coccidial protozoa having a tough outer coat. In its initial formation the core of the oocyst is in an immature state not having as yet elements of infective capability and may be referred to as an "unsporulated oocyst." Such "oocysts" are found in the gut of animals prior to elimination or on the ground just after elimination.

4.2 A "sporulated oocyst" is an oocyst which has undergone biochemical maturation brought about naturally or artifically under certain temperature and oxygen exposure conditions. One common artificial sporulating condition is exposure to dichromate solution. During maturation a multiplicity of "sporocysts" each within its own case or shell develops within the outer case thus becoming "cysts within a cyst." In the instance of the chicken, e.g., *E. tenella*, have four separate encased sporocysts within the outer shell after the oocyst have undergone sporulation. Live sporulated oocysts are commonly referred to as "viable sporulated oocysts."

4.3 "Encysted coccidial protozoa," "encysted oocysts" and "encysted sporocysts" all refer to organisms which are within the cyst or have their own natural shell or sporecase.

4.4 Each sporocyst shell surounds the ultimate infective agent, the "sporozoite." In the instance of *E. tenella* each sporocyst shell encompasses two sporozoites.

4.5 The term "excysted sporozoite" refers to the live sporozoite from which the protecting shell of the sporocyst has been removed. Excystation occurs naturally by biochemical reaction but is accomplished, for use of the excysted sporozoites, in the method of this invention by homogenization of a suspension of pure sporulated oocysts, centrifuging to remove solubles, treating the solids with a solution of trypsin and taurodeoxycholic acid in Hank's solution at pH 7.4 followed by purification using anion exchange chromatography as described more fully infra. Methods of obtaining sporozoites as described herein bypass isolation of sporocysts as such.

4.6 "Capsule Wall Material" refers to outer hardened surface of the microcapsule which results from cross-linking of the water soluble polymeric stabilizer with a suitable cross linking agent.

4.7 Suitable "cross-linking agents" are divalent cations in the instance of polysaccharide gums, and aldehydes such as glutaraldehyde or formaldehyde in the instance of gels and gelatins.

4.8 "Water soluble polymeric stabilizers" or "Polymeric stabilizers" and "viscosity enhancing substances" all refer generally to gels, gelatins, cellulose, cellulose derivatives and polysaccharide gums, one or more of which are required in the compositions of this invention. Included in this group of materials are alginates of high and low viscosity, acacia, agar, agarose, albumen, dextran, various gelatins, polyvinyl alcohol, sodium carboxycellulose and starches.

The specific way in which these materials function to stabilize the sporozoites and increase longevity is not known, however, a suitable viscosity range for prolonging sprorozoite stability (viability) in suspensions of this invention is 100–400 centipoises as measured at about 25° C.

4.9 The term "modified capsule wall" as used herein refers to the microcapsule shell, e.g., calcium alginate, having been formed which has been treated after formation, usually after storage and prior to administration to allow easier escape of sporozoites from the microcapsule. Suitable capsule wall modifiers for the alginate system are salts of weak acids such as critric acid, fumaric acid and maleic acid.

4.10 By the use of the term "physiologically balanced," when used in conjunction with the compositions herein described, is meant the compositions are physiologically balanced with respect to isotonicity and pH of living cells, the pH being in the range of 6.8 to 7.5; preferably about 7.2 and having osmolality in the range of 260–350 milliosmoles. The suspension of sporozoites are thus buffered to physiological pH and osmotically balanced with respect to living cells. Generally amine buffers may be used to physiologically balance, for example, TRIS buffer and HEPES buffer are effective buffering agents.

4.11 The term "suspension" as used herein refers to both liquid and solid suspensions, should the latter occur within the microcapsule.

5.

DETAILED DESCRIPTION OF THE INVENTION 5.1 Scope and Applicability

Compositions useful in the vaccination procedure for the invention may contain sporozoites of a single strain or species of coccidia; however when broad host-specific immunity is required, a selection of sporozoites of common strains or species of coccidia should be included in a single formulation.

The invention may be applied to the control of coccidiosis in any animal host species that is prone to the disease. In addition to the avian species, pigs and ruminants such as cattle, sheep, goats and rabbits are affected by the disease and may all benefit from use of the method of this invention.

In chickens about seven major species of coccidial parasitize the intestinal tract beginning with the duodenum; they are: *Elimeria acervulina, E. mivati, E. Maxima, E. necatrix, E. brunetti, E. mitis,* and *E. tenella.* In turkeys, the following coccidia have been observed: *E. melagrimitis, E. disperse, E. meleagridis, E. gallopavonis, E. adenoides, E. innocus* and *E. scubrotunda.* In pigs the following coccidia have been observed: *E. debliecki, E. scabra, E. suis, E. spinosa, E. perminuta, E. neodebliecki, E. porci, E. cerdonis, E. polita* and *Isospora suis.* In cattle the following coccidia have been observed: *E. bovis, E. zuernii, E ellipsoidalis, E. auburnersis, E. cyclindrica, E. alabamensis* and *E. bukidnonensis.* In sheep, the following coccidia have been observed: *E. minokohlyakimovae, E. ovina, E. intricate* and *E. aheate.* Goats are infected by *E. arloinge* and rabbits are infected by *E. intestinalis, E. flavesens, E. magna, E. irresidua, E. periformis, E. stiedai, E. performans, E. neoleporis* and *E. media.*

5.2 Preparation 1. Excysted *E. tenella* Sporozoites in Buffer Solution 5.2.1 General Procedure for Isolating Excysted Sporozoites The procedure used to obtain purified *Elimeria tenella* sporozoites was that of Schmatz, D.M. et al. described in J. Protozol 31(1)(1984) pp. 181-183 hereby and herein incorporated by reference and described stepwise in abbreviated form following. In addition microscopic observation was employed from time to time.

5.2.2 Obtaining Precursor Sporulated Oocysts

Coalesced masses of oocysts were isolated by scraping cercal pouches of chickens which had been infected seven days earlier with *Eimeria tenella* (A. H. Robins strain 855). The cecal cores in distilled water were disrupted in a Waring Blender ® and digested with pepsin at pH 2.0 and 39° C. for 1 hr. Debris and pepsin were removed by centrifugation in distilled water. A partially purified oocyst fraction was isolated by flotation in 1.1 molar aqueous sucrose solution. This semi-pure oocyst fraction was incubated in cold Chlorox ® solution for 15 min at 4° C. The Chlorox ® component was removed by washing several times in sterile phosphate buffered saline (PBS) at pH 7.3. The resulting purified sterile viable oocysts were suspended in dichromate solution and then sporulated by shaking in a water bath at 29° C. for 48 hr. The sporulated oocysts in PBS were stored at 4° C. until used in the next step.

5.2.3 Excystation of Sporozoites and Buffered Solution Thereof

A 2 ml suspension of PBS (pH 7.3) as prepared above containing sporulated oocysts, was ground in a tissue homogenizer operated at about 500 rpm for 5 min at 4° C. Soluble material resulting from disruption of the sporulated oocysts was removed by centrifugation. The pellet obtained, composed of unbroken oocysts, sporocysts and oocyst shells, was resuspended in excysting solution which contained as excysting agents: 0.25% (weight/volume) trypsin (1:250) and 4% (weight/volume) taurodeoxycholic acid (Sigma Co., St. Louis, Mo.) in Hank's balanced salt solution (pH 7.4). The mixture was incubated in an atmosphere of 5% carbon dioxide at 41° C. for 1 hr. The excysting solution was removed by two washes with stock column buffer solution. Column buffer solution for this and subsequent column purification was prepared as follows: A stock buffer solution of 2×phosphate-buffered saline (2×PBS, 26.96 g/liter disodium phosphate, 1.56 g/liter disodium phosphate, 8.5 g/liter sodium chloride) was used to prepare a solution 2:8 (vol/vol) PBS:H$_2$O of 0.145 ionic (I) strength.

5.2.4 Chromatographic Purification of Excysted Sporozoites

The excysted sporozoites in buffer solution were purified using anion exchange column chromatography in specially prepared cellulose (DE-52 cellulose) packed column as described by Schmatz, ibid, the appearance of the solution under the microscope confirming the completeness of the purification.

DE-52 cellulose anion exchange column packing was prepared by equilibrating per-swollen Whatman (England) DE-52 cellulose in proportions of 2.0 g in 150 ml of the 2:8 buffer (I=0.145). After settling, the supernatent containing the fines was removed. This washing procedure was repeated twice more and the DE-52 cellulose was adjusted to pH=8.0 with 5% (wt/vol) phosphoric acid prior to the last wash. This material was then resuspended in 50 ml of the 2:8 buffer and used to fill the column.

The columns used to purify excysted sporozoites were sterilized by autoclaving prior to filling. Columns were packed to a height of 2.5 cm with the DE-52 cellulose, as prepared above, and the packing was rinsed with 50 ml of 2:8 buffer (I=0.145).

Freshly excysted sporozoites as prepared above in 2.8 buffer were loaded onto a column loaded with 2:8 equilibrated DE-52 cellulose, as prepared above. Portions of 2:8 buffer were sequentially passed through the column. The portions were collected off the column and the content evaluated and quantified by hemocytometer under phase microscopy. The suspension of excysted sporozoites in buffered solution thus obtained was suitable for adding to solutions containing stabilizers described herein such as sodium alginate solutions.

5.3 Preparation 2. Suspension of Excysted *E. tenella* Sporozoites in Isotonic Buffered Aqueous Sodium Alginate Solution The following is a stepwise description of preparation of alginate-stabilized suspensions of sporozoites suitable as vaccine to be used directly or microencapsulated.

5.3.1 TRIS Buffer Solution 0.1M solution of TRIS Buffer [Tris (hydroxymethyl-)aminomethane] was prepared by accurately weighing 6.057 g of TRIS crystals and diluting with 500 ml of distilled water.

5.3.2 Buffered Sodium Alginate Solution 1.5% sodium alginate (low viscosity) solution was prepared by dissolving 7.5 g of sodium alginate in 500 ml of TRIS buffer prepared above. The solution is cooled to 4° C.

5.3.3 CalfSerum Addition

Freshly prepared concentrated suspension having $1\times10^8$ sporozoites in 5 ml of TRIS buffer was obtained (from Preparation 1) and 5 vol % fetal calf serum was added and the suspension was kept at 4° C.

5.3.4 Buffered Sporozoite-Alginate Suspension

The 5 ml of buffered solution containing the $1\times10^8$ sporozoites in 5.3.3 above was added to 145 ml of the alginate solution prepared in 5.3.2 above with stirring until blending was complete. The suspension of sporozoites was then maintained at 4° C. These proportions were based on microencapsulation needs in Preparation 3 wherein calcuations are explained.

5.4 Preparation 3. Microcapsules Containing Stabilized Excysted *E. tenella* Sporozoites in Isotonic Buffered Aqueous Solution The following is a description of the procedure for encapsuating the stabilized suspension of excysted sporozoites:

5.4.1 Calculations on Volume Ratios

The proportion of buffered sodium alginate solution to buffered sporozoite suspension used to prepare the product of Preparation 2 was based on calculation to produce microcapsules of a certain size using the formula below using the following facts and assumptions: (1) that 5 ml of buffered sporozoite suspension contained $1 \times 10^8$ sporozoites, (2) that microcapsules of 350 micron diameter would be prepared, (3) that it was the aim to have each microcapsule contain 15 sporozoites and (4) that based on the radius of 175 microns and the formula for calculating the volume of a sphere $(4/3\ \pi r^3)$ there would be 44,545 microcapsules per ml of final alginate solution.

$$1 \times 10^8 \text{ sporozoites} \times \frac{1 \text{ microcap}}{15 \text{ sporozoites}} \times$$

$$\frac{1 \text{ ml alginate suspension}}{44,545 \text{ microcapsules}} = 150 \text{ ml of final alginate suspension}$$

Therefore 145 ml of the alginate solution was added to 5 ml of buffered solution containing the $1 \times 10^8$ sporozoites prepared in Preparation 2.

5.4.2 Preparation of Hardening Bath

A hardening bath of 1.5% calcium chloride solution was prepared by dissolving 19.63 g of calcium chloride dihydrate (76.4% calcium chloride) in 1 liter of distilled water. The osmolality of this solution was about 335 miliosmoles/kg.

5.4.3 Description of Gas Flow Droplet Generator (Jet-Spray Head)

The jet spray head used to finely divide the sodium alginate sporozoite suspension was mounted above the hardening bath and perpendicularly lengthwise to the bath surface.

The jet-spray head consisted of a housing having a small elongated conical chamber $\frac{3}{4}''$ in height $\times \frac{1}{4}''$ ID. at the top and 1/16" ID at the bottom, capped with a rubber disc at the top broader end and open at the narrower end, the chamber having a side gas port and a liquid feed needle protruding through the cap and downward through the length of the chamber so that the open end of the needle extended well into the chamber. A pump was used to regulate liquid flow through the needle and a gas pressure valve was used to control gas flow into the chamber via the sideport. The needle used was a 21 gauge $\times 1\frac{1}{2}''$ syringe needle with a conically shaped tip.

5.4.4 Preparation of Microcapsules Containing Sporozoites Suspended in Stabilizing Aqueous Solution With the bottom end of the jet-spray head set about 1.5 cm above the hardening bath, the sporozoite-alginate suspension from Preparation 2 under constant agitation at 4° C. was pumped with a peristaltic pump at a flow rate of 0.46 ml/min against a gas flow through the side port of about 8 liters per min, the microspheres being blown off into the hardening bath. The size of the microspheres was adjusted to about 350 micron diameter, using microscopic examination of the microcapsules being obtained to determine the size, by manipulating the gas flow rate and the position of the needle opening. The microspheres immediately hardened on entering the bath. This batch of microcapsules utilized 135 ml of the starting 150 ml of sporozoite suspension described above to give a total of $1 \times 10^6$ microcapsules.

5.4.5 Washing of Micocapsules with Saline

The microcapsules prepared above were allowed to settle to a stable volume in the hardening bath and excess calcium chloride was decanted off. The residual microcapsules, wet with calcium chloride solution were resuspended in an equivalent volume of normal saline, i.e., aqueous 0.9 wt % sodium chloride solution, at 4° C. and allowed to settle again. The washing process was repeated three times. The microcapsules in normal saline were then refrigerated at about 4° C. until they were used as vaccine or modified and used as vaccine as in paragraph 5.9 below.

5.4.6 Storage Tests Relative to Viability of Microencapsulated Sporozoites

The microcapsules as prepared in 5.4.5 in normal saline were stored for 5 weeks at 4° C. The saline was decanted and the microcapsules were resuspended in PBS solution (pH=7.3). The suspension was administered subcutaneously in the back of the neck to one week old Hubbard $\times$ Hubbard male chicks. The chicks were sacrificed 7 and 8 days after administration and cecal pouches found to be infected with coccidia. It is concluded therefore that sporozoites contained in a suspension of physiologically compatible medium containing an alginate salt, the whole of which suspension of sporozoites is microencapsulated by crosslinking the alginate with a divalent cation, remained viable for at least 5 weeks when stored in normal saline at 4° C.

5.5 Example 1. Demonstration of Sub-Clinical Infection With Microencapsulated and Unencapsulated Sporozoites of *E. tenella* in Chickens A short initial study affirmed that low-level infection could be obtained with both unencapsulated live excysted sporozoites as obtained in Preparation 2, and microencapsulated live excysted sporozoites as obtained in Preparation 3. Four groups of one-day old chickens were sacrificed after 7 or 8 days exposure and their cecal pouches were examined for lesions. The study is summarized in Table I.

TABLE I

Demonstration of Infectability With Microencapsulated Sporozoites

| Group No. | Number of Chickens In Group | Sporozoite Treatment Kind | Method of Administration (a) | Cecal Infection Observed on Day: Day 7 | Day 8 |
|---|---|---|---|---|---|
| 1 | 15 | microcaps, $10^5$ live excysted sporozoites | S.Q. (back of neck) | lesions 7/8 | lesions 8/8 |
| 2 | 9 | $10^5$ live excysted sporozoites, no encapsulation | S.Q. (back of neck) | lesions 7/9 | — |

TABLE I-continued

Demonstration of Infectability With Microencapsulated Sporozoites

| Group No. | Number of Chickens In Group | Sporozoite Treatment Kind | Method of Administration (a) | Cecal Infection Observed on Day: Day 7 | Day 8 |
|---|---|---|---|---|---|
| 3 | 9 | $10^5$ live excysted sporozoites, no encapsulation | i.p. | lesions 8/9 | — |
| 4 | 10 | none (controls) | — | no lesions 10/10 | — |

(a)S.Q. = subcutaneously on back of neck
i.p. = intraperitoneally 5.6 Example 2, Demonstration of Vaccination Potential Against *E. tenella* Coccidia Using Microencapsulated Excysted Stabilized Sporozoites In Chickens Two hundred and forty (240) one-day old Hubbard-×Hubbard broiler chicks were divided into four groups, chickens being randonly selected so that their body weights were within 10% of the mean. Groups 1 and 2 were in replicates of 2 floor pens, each pen housing 40 chicks for a total of 80 chicks in each of groups 1 and 2. Groups 3 and 4 were in single pens housing 40 chicks per pen. Each group of chicks were individually injected subcutaneously (S.Q.) in the back of the neck on day one as follows:

Group 1: Each chick received S.Q. microencapsulated PBS-sodium alginate suspension of 105 live excysted sporozoites, the microcapsules being suspended in normal saline, volume totalling 0.1 ml. The microcapsules were those prepared in Preparation 3.

Group 2: Each chick received S.Q., microencapsulated PBS-sodium alginate suspension of $5 \times 10^3$ live excysted sporozoites, the microcapsules being suspended in normal saline, volume totalling 0.1 ml. The microcapsules were those prepared in Preparation 3.

Group 3: Each chick received subcutaneously, PBS suspension of $10^5$ live freshly excysted sporozoites in 0.1 ml volume. See Preparation 1 for procedure of obtaining sporozoites. No microencapsulation was involved.

Group 4: Each chick received 0.1 ml of PBS solution only.

Twenty eight days later each chick was fed an oral challenge of 85,000 *E. tenella* oocysts.

On Day 34 (i.e. 6 days after the oocyst challenge) the chicks were sacrificed and both cecal pouches of each chick were examined for damage to the cecal walls using the scoring procedure of Joyce Johnson and W. Malcolm Reid described in Experimental Parasitology 28, 30–36 (1970) on page 31 for *E. tenella* with grading scores applicable as follows:

Grading Score:

0 No gross lesions

+1 Very few scattered petechiae on the cecal wall; no thickening of the cecal walls; normal cecal contents present.

+2 Lesions more numerous with noticeable blood in the cecal contents; cecal wall is somewhat thickened; normal cecal contents present.

+3 Large amounts of blood or cecal cores present; cecal walls greatly thickened; little if any fecal contents in the ceca.

+4 Cecal walls greatly distended with blood or large caseous cores; fecal debris lacking or included in cores. Dead birds scored as +4.

Table II summarizes important features of the test and shows net cumulative results of the test on each group as a percentage of all individuals exhibiting a low scoring range 0–1.5, a middle scoring range 2–2.5 or a high scoring range 3–4. As will be readily realized by one skilled in the art, a high percentage in the low scoring range of 0–1.5 is desirable and is indicative of the effectiveness of the vaccination procedure.

TABLE II

Immunication Studies With Microencapsulated Excysted *E. tenella* Sporozoites In Chickens (Example 2 Summary)

| Group No. | No. of Chickens Per Group | Day 1: Sporozoite Treatment Subcutaneous(a) | Day 28: Oocyst Challenge Oral | Day 34: Cecal Damage 6 days after Oocyst Challenge, % of Chickens in Scoring Ranges of: 0–1.5 (low) | 1.75–2.5 | 3–4 (high) |
|---|---|---|---|---|---|---|
| 1 | 2 pens of 40 each | microencapsulated PBS alginate suspension of $10^5$ sporozoites(b) | 85,000 Sporulated oocysts | 42 | 18 | 40 |
| 2 | 2 pens of 40 each | microencapsulated PBS alginate suspension of $5 \times 10^3$ sporozoites(b) | 85,000 Sporulated oocysts | 11 | 10 | 79 |
| 3 | 1 pen of 40 | freshly prepared suspension of $10^5$ sporozoites(b) | 85,000 Sporulated oocysts | 93 | — | 5 |
| 4 | 1 pen of 40 | PBS 0.1 ml vol (no sporozoites) | 85,000 Sporulated oocysts | 9 | 16 | 75 |

(a)Subcutaneous in back of neck
(b)Microcapsules in 0.1 ml vol. with normal saline 5.7 Example 3. Demonstration of Vaccination Potential Against *E. tenella* Coccidia Using Microencapsulated Excysted Stabilized Sporozoites In Chickens Three hundred and sixty (360), one-day old Hubbard-×Hubbard broiler chicks were divided into 18 pens of 20 chicks each, randomly selected so that their body weights were within 10% of the mean. The eighteen groups were randomly divided into 3 pens each for 6 treatment groups. Groups 1-5 were adjacently located and Group 5 was in a separate area. The treatment groups were as follows: Treatment for each group on day one was as follows:

Group 1: Each chick in 3 pens received, S.Q., 2 week old microencapsulated PBS suspension of $1 \times 10^5$ live excysted *E. tenella* sporozoites, the microcapsules being suspended in normal saline, volume totalling 0.1 ml. The microcapsules were prepared by a procedure similar to that of Preparation 3, of about 250 micron average size.

Group 2: Same as Group 1 except administration was intraperitoneally (i.p.) to chicks in 3 pens.

Group 3: Freshly prepared $1 \times 10^5$ excysted *E. tenella* sporozoites - PBS suspension was administered S.Q., to chicks in 3 pens (0.1 ml).

Group 4: Same as group 3, except suspension of sporozoites was administered intraperitoneally to chicks in 3 pens (0.1 ml).

Group 5: 0.1 ml of PBS solution only was administered S.Q., to chicks in 3 pens.

Group 6: Three pens of chicks were kept isolated, no treatment given.

Twenty seven days later each chick was fed an oral challenge of 50,000 *E. tenella* oocysts.

On day 33 (=6 days after the oocyst challenge) the chicks were sacrificed and both cecal pouches of each chick were examined for damage to the cecal walls using the scoring procedure of Joyce Johnson and W. Malcolm Reid described in Example 2 herein.

Table III summarizes important feature of the test and shows net cumulative results of the test on each group as a percentage of all individuals exhibiting scoring ranges of 0-1.5, 2-2.5 and 2.75-4.

5.8 Example 4. Stabilizing Effect of Sodium Alginate on *E. tenella* Sporozoites To 200 ml of a 1.5% solution of sodium alginate (low viscosity) was added 1 ml of a freshly prepared suspension having $10^6$–$10^7$ sporozoites/ml in TRIS buffered solution containing calf serum as prepared in par.5.3.3 so as to give a suspension of 5,000 excysted sporozoites/ml. After 14 days storage at 4° C., chicks were injected per cloacal with 0.2 ml (1000 sporozoites) of the suspension. Infective ability was still present at that time (examination of cecal pouches for lesions) whereas sporozoites in TRIS buffer containing calf serum had no infective ability after 14 days storage at 4° C.

5.9 Example 5. Vaccination Potential Using Microcapsules Having Capsule Wall Modified with Citrate Microcapsules prepared from alginate as in paragraph 5.4, supra, and suspended in isotonic solution and stored at 4° C. for periods of time up to 5 weeks were mixed with a 1.5% aqueous sodium citrate solution at pH 7.2 for a period of time of 1-2 minutes. Using a microscope, liberation of sporozoites was observed. The suspension, so treated, when administered subcutaneously to newly hatched chicks is expected to give improved innoculation against *E. tenella* oocyst challenge compared to the unmodified microcapsules due to greater efficiency and speed of sporozoite release from the microcapsule.

What is claimed is:

1. A composition for vaccinating warm-blooded animals against coccidiosis disease comprised of a suspension of live excysted coccidial sporozoites in aqueous medium, physiologically balanced with respect to isotonicity and pH, containing at least one water-soluble viscosity enhancing polymeric substance selected from hydrosols, gels, gelatins, cellulose, cellulose derivatives and polysaccharide gums in amount sufficient to significantly prolong viability of said sporozoites.

2. The composition of claim 1 wherein the water-soluble polysaccharide gum is sodium alginate.

3. The composition of claim 1 wherein the sporozoites are of the species *Eimeria tenella*.

4. A composition for vaccinating warm-blooded animals against coccidiosis disease comprised of microcap-

TABLE III

Immunization Studies with Microencapsulated Excysted *E. tenella* Sporozoites in Chickens(Example 3 Summary)

| Group No. | No. of Chickens Per Group | Day 1: Sporozoite Treatment (Route) | Day 28: Oocyst Challenge Oral | Day 34: Cecal Damage 6 days after Oocyst Challenge, % of Chickens in Scoring Ranges of: | | |
|---|---|---|---|---|---|---|
| | | | | 0-1.5 | 2.0-2.5 | 2.75-4 |
| 1 | 3 pens of 20 each | microencapsulated PBS suspension of $10^5$ sporozoites(S.Q.) | 50,000 oocysts | 43 | 38 | 19 |
| 2 | 3 pens of 20 each | microencapsulated PBS suspension of $10^5$ sporozoites(i.p.) | 50,000 oocysts | 50 | 25 | 25 |
| 3 | 3 pens of 20 each | $10^5$ freshly prepared sporozoites in PBS(S.Q.) | 50,000 oocysts | 90 | 10 | 0 |
| 4 | 3 pens of 20 each | $10^5$ freshly prepared sporozoites in PBS(i.p.) | 50,000 oocysts | 94 | 0 | 6 |
| 5 | 3 pens of 20 each | PBS Solution only(S.Q.) | 50,000 oocysts | 30 | 35 | 35 |
| 6 | 3 pens of 20 each (Isolated) | None | None | 5 | 20 | 75 | sules containing internally, inside the microcapsule wall, a suspension of live excysted coccidial sporozoites, physiologically balanced with respect to isotonicity and pH containing at least one water-soluble viscosity enhancing polymeric substance selected from hydrosols, gels, gelatins, cellulose, cellulose derivatives and polysaccharide gums in amount sufficient to significantly prolong viability of said sporozoites and said microcapsule wall comprised of hardened polymeric substance.

5. The composition of claim 4 wherein the water-soluble polysaccharide gum is sodium alginate and the microcapsule wall is calcium alginate.

6. The composition of claim 4 wherein the sporozoites are of the species *Eimeria tenella*.

7. A composition comprised of a suspension of excysted coccidia sporozoites, physiologically balanced with rspect to isotonicity and pH, containing sodium alginate in solution, said composition having a viscosity in the range of 100–400 centipoises at 25° C.

8. The composition of claim 7 wherein the species of sporozoites is *Eimeria tenella*.

9. A method of vaccinating warm-blooded animals against coccidiosis disease by administering to said animal a composition comprised of a suspension of live excysted coccidial sporozoites, physiologically balanced with respect to isotonicity and pH containing at least one water-soluble viscosity enhancing polymeric substance selected from hydrosols, gels, gelatins and polysaccharide gums in amount sufficient to significantly prolong viability of said sporozoites.

10. The method of claim 9 wherein the water-soluble polysaccharide gum is sodium alginate.

11. The method of claim 9 wherein the animal is a chicken.

12. The method of claim 9 wherein the animal is a chicken and the composition is administered subcutaneously in the back of the neck.

13. A method of vaccinating warm-blooded animals against coccidiosis disease by administering to said animal a composition comprised of microcapsules containing internally, inside the microcapsule wall, a suspension of live excysted coccidial sporozoites, physiologically balanced with respect to isotonicity and pH and containing said suspension containing at least one water-soluble viscosity enhancing polymeric substances selected from hydrosols, gels, gelatins, cellulose, cellulose derivatives and polysaccharide gums, said polymeric substance being in amount sufficient to significantly prolong viability of said sporozoites and said microcapsule wall comprised of hardened polymeric substance.

14. The method of claim 13 wherein the water-soluble polysaccharide gum used is sodium alginate and the microcapsule wall is calcium alginate.

15. The method of claim 13 wherein the sporozoites are of the species *Eimeria tenella*.

* * * * *